United States Patent
Bruegl et al.

(10) Patent No.: US 11,440,552 B2
(45) Date of Patent: Sep. 13, 2022

(54) METHOD AND DEVICE FOR OPERATING AN ASSISTANCE SYSTEM IN A MOTOR VEHICLE

(71) Applicant: Bayerische Motoren Werke Aktiengesellschaft, Munich (DE)

(72) Inventors: Juergen Bruegl, Munich (DE); Matthias Franz, Groebenzell (DE); Michael Hellmuth, Bad Staffelstein (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 111 days.

(21) Appl. No.: 16/649,738

(22) PCT Filed: Nov. 6, 2018

(86) PCT No.: PCT/DE2018/100897
§ 371 (c)(1),
(2) Date: Mar. 23, 2020

(87) PCT Pub. No.: WO2019/086082
PCT Pub. Date: May 9, 2019

(65) Prior Publication Data
US 2020/0262440 A1 Aug. 20, 2020

(30) Foreign Application Priority Data

Nov. 6, 2017 (DE) ...................... 10 2017 219 676.9
Mar. 16, 2018 (DE) ...................... 10 2018 204 103.2

(51) Int. Cl.
*B60W 40/08* (2012.01)
*B60W 30/08* (2012.01)

(52) U.S. Cl.
CPC ............ *B60W 40/08* (2013.01); *B60W 30/08* (2013.01); *B60W 2040/0881* (2013.01)

(58) Field of Classification Search
CPC ....... A61L 2209/111; A61L 2209/00–2209/22; F24F 2110/60; F24F 2110/00–2110/65;
(Continued)

(56) References Cited

U.S. PATENT DOCUMENTS 5,450,894 A 9/1995 Inoue et al.
7,559,610 B1* 7/2009 Hong Min ............. A47C 7/744
297/180.1

(Continued)

FOREIGN PATENT DOCUMENTS

CN 203753082 U 8/2014
CN 105574448 A 5/2016
(Continued)

OTHER PUBLICATIONS

International Search Report (PCT/ISA/210) issued in PCT Application No. PCT/DE2018/100897 dated Feb. 12, 2019 with English translation (five pages).

(Continued)

*Primary Examiner* — Fadey S. Jabr
*Assistant Examiner* — Mohamed Abdo Algehaim
(74) *Attorney, Agent, or Firm* — Crowell & Moring LLP

(57) ABSTRACT

A method for operating an assistance system in a motor vehicle detects at least one odor profile using a respective odor sensor. The at least one odor profile is defined by concentrations of at least two odorous substances. The method carries out one or more assistance functions depending on the detected at least one odor profile.

10 Claims, 2 Drawing Sheets

(58) Field of Classification Search
CPC ......... Y02B 30/70; Y02B 30/00–30/90; B60N 2/005; B60N 2/002; B60N 2/976; B60N 2/00–2/995; B60W 40/08; B60W 30/08; B60W 2040/0881; B60W 2540/26; B60W 2540/221; B60W 2540/24; B60W 2040/0818; B60W 2040/0836; B60W 2040/0845; B60W 2040/0872; B60W 30/00–2030/206; B60W 40/00–2040/1392; B60K 28/066; B60K 28/00–28/165
USPC .......................................................... 701/36
See application file for complete search history.

(56) References Cited

U.S. PATENT DOCUMENTS

| | | | | |
|---|---|---|---|---|
| 11,074,465 | B2* | 7/2021 | Wright | G06K 9/00617 |
| 2004/0053571 | A1* | 3/2004 | Aoki | B60H 3/0007 |
| | | | | 454/159 |
| 2009/0081938 | A1* | 3/2009 | Kim | B60H 1/00285 |
| | | | | 454/75 |
| 2010/0294583 | A1* | 11/2010 | Biondo | A61B 5/082 |
| | | | | 340/576 |
| 2013/0054090 | A1* | 2/2013 | Shin | B60K 28/06 |
| | | | | 701/36 |
| 2016/0191511 | A1 | 6/2016 | Tijerina et al. | |
| 2016/0354027 | A1* | 12/2016 | Benson | A61B 5/1102 |
| 2017/0050750 | A1* | 2/2017 | Barraci | G07C 5/006 |
| 2017/0263098 | A1* | 9/2017 | Garcia | G08B 21/0202 |
| 2017/0369168 | A1* | 12/2017 | Hwang | A61L 9/14 |
| 2018/0008855 | A1* | 1/2018 | Yanev | A63B 24/0062 |
| 2018/0074495 | A1* | 3/2018 | Myers | G06Q 50/30 |
| 2018/0194194 | A1* | 7/2018 | Lyubich | B60N 2/5628 |
| 2018/0225551 | A1* | 8/2018 | Lin | B60H 3/0035 |
| 2018/0281627 | A1* | 10/2018 | Ali | B60N 2/2812 |
| 2019/0061466 | A1* | 2/2019 | MacNeille | B60H 1/00821 |
| 2019/0129416 | A1* | 5/2019 | Upmanue | B60W 40/08 |
| 2019/0273817 | A1* | 9/2019 | Ueno | G08G 1/166 |
| 2020/0385025 | A1* | 12/2020 | Nishimura | G06V 20/597 |

FOREIGN PATENT DOCUMENTS

| | | | |
|---|---|---|---|
| CN | 207725220 U | * | 8/2018 |
| CN | 109425578 A | | 3/2019 |
| DE | 692 21 263 T2 | | 11/1997 |
| DE | 198 41 814 A1 | | 3/2000 |
| DE | 103 39 002 A1 | | 3/2004 |
| DE | 10 2009 021 959 A1 | | 11/2010 |
| DE | 10 2015 210 055 A1 | | 12/2016 |
| WO | WO 2017/134255 A1 | | 8/2017 |

OTHER PUBLICATIONS

German-language Written Opinion (PCT/ISA/237) issued in PCT Application No. PCT/DE2018/100897 dated Feb. 12, 2019 (five pages).

German-language Search Report issued in German Application No. 10 2018 204 103.2 dated Jul. 23, 2018 with partial English translation (13 pages).

Chinese-language Office Action issued in Chinese Application No. 201880071486.4 dated Nov. 2, 2021 with English translation (18 pages).

Korean-language Office Action issued in Korean Application No. 10-2020-7015444 dated Jan. 22, 2022 with English translation (seven (7) pages).

* cited by examiner

METHOD AND DEVICE FOR OPERATING AN ASSISTANCE SYSTEM IN A MOTOR VEHICLE

BACKGROUND AND SUMMARY OF THE INVENTION

The invention relates to motor vehicles, in particular having assistance systems for supporting a driver and/or further vehicle occupants during a journey.

Assistance systems in motor vehicles respond in many ways to the state of the driver or other vehicle occupants and control vehicle functions accordingly. By way of example, a fatigue assistant may recognize fatigue of the driver by evaluating steering movements and/or by observing the eye area and accordingly output warnings or adjust vehicle functions.

Sensors are often also installed in vehicle seats and recognize seat occupancy or the contour, body size and the like of a person sitting thereon, and control corresponding functions of the vehicle seat and/or of the vehicle. Sensors for recording a temperature of the vehicle seat or for recording other vital parameters of vehicle occupants may also perform detection, such as for example an ECG sensor system for monitoring heart activity, and operate vehicle functions accordingly.

The sensor system used up until now to record vital parameters comprises only some of the options, and the object of the present invention is therefore to record a more comprehensive recognition of a state of a driver and/or further vehicle occupants in a motor vehicle and to take this into consideration in order to execute assistance functions while the vehicle is occupied.

This object is achieved by the method for operating an assistance system in a motor vehicle and by the assistance system, the vehicle seat and the motor vehicle according to the claimed invention.

According to a first aspect, what is provided is a method for operating an assistance system in a motor vehicle, having the following steps:

recording at least one odor profile by way of a respective odor sensor, wherein the at least one odor profile is defined by concentrations of at least two odorants;

performing one or more assistance functions depending on the recorded at least one odor profile.

One concept of the above method is that of evaluating the body odor, that is to say odorants given off via the skin or breath, of a vehicle occupant, in particular of a driver of the motor vehicle, and drawing a conclusion as to the physiological state or the change in the state of the user depending on the odor profile or a change in the odor profile. These changes may be for example the onset of fatigue or a change in a stress level caused by a previous stressful situation. Using the odor profile or the change in the odor profile, it is possible to draw a conclusion as to a state or a change in the state, in particular a change in a pressure state of a vehicle occupant, in a manner that has been determined beforehand. The odor composition, that is to say the composition of the odorants in the odor profile, may also be used to identify a particular user in order thus to be able to perform individual presetting or individual execution of vehicle functions in a manner adjusted to the user.

Odor sensors in this document are understood in the broader sense to be sensors that are suitable for detecting one or more chemical substances able to be given off by the human body into ambient air. In this case, the chemical substances may comprise odorants that are able to be perceived intentionally, unintentionally or not at all.

The evaluation of the odors given off by occupants of a motor vehicle, such as for example odorants given off via the skin, in relation to the odorants given off via the breath, may be used to specify or determine the state of a vehicle occupant using further measures beyond the previous methods.

At least two odor sensors may furthermore be assigned to different vehicle seats of the motor vehicle, such that an odor profile of a user sitting on the respectively assigned vehicle seat is able to be recognized, wherein seat occupancy is recognized by comparing the odor profile assigned to the vehicle seat in question with a predefined reference odor profile of ambient air, wherein the one or more assistance functions are performed depending on the recognized seat occupancy.

The reference odor profile may in particular be recorded by a reference odor sensor.

There may be provision for the at least one odor profile to be assigned to a particular user by way of a predefined user reference odor profile, wherein the one or more assistance functions may be performed or adjusted individually depending on the particular user, wherein information about the user reference odor profile is in particular stored in the assistance system and/or is received externally from the vehicle.

The odor profile may furthermore be recorded over time, wherein a change in the odor profile is recognized depending on the recorded temporal evolution of the odor profile and this is assigned to a state change of a user, wherein the one or more assistance functions are performed depending on the state change.

There may furthermore be provision, after performing the one or more assistance functions depending on the recorded at least one odor profile, to furthermore stop the performance of the one or more assistance functions or to adjust the performance of the one or more assistance functions depending on a further change in the odor profile. The success of a measure is thereby able to be checked in order to continue applying the assistance function in question if this has changed the state of the vehicle occupant. Thus, for example when activating a massage function as assistance function, the massage function may continue to be applied in the case of a corresponding change in the odor profile if a change/improvement in the state is identified through the change in the odor profile of the vehicle occupant in question, or the massage function may accordingly no longer be applied in the case of a corresponding change in the odor profile if no change in the odor profile or no change/improvement in the state is identified as a result.

If a change in state was not conducive, then proven measures are resorted to in the event of the next comparable state of the vehicle occupant.

According to a further aspect, what is provided is an assistance system in a motor vehicle, wherein the assistance system is designed:

to record at least one odor profile by way of a respective odor sensor, wherein the at least one odor profile is defined by concentrations of at least two odorants;

to perform one or more assistance functions depending on the recorded at least one odor profile.

According to a further aspect, a vehicle seat is equipped/provided with at least one odor sensor that is arranged in a backrest, a head support and/or a seat surface.

According to a further aspect, a motor vehicle is equipped with the above assistance system and with the above vehicle seat and/or with an odor sensor assigned to the vehicle seat, in particular in the roof lining.

The above motor vehicle may furthermore be provided with a reference odor sensor in order to record an odor profile of ambient air fed into an interior of the motor vehicle.

BRIEF DESCRIPTION OF THE DRAWINGS

Embodiments are explained in more detail below with reference to the attached drawings, in which.

DETAILED DESCRIPTION OF THE DRAWINGS

Figure 1:
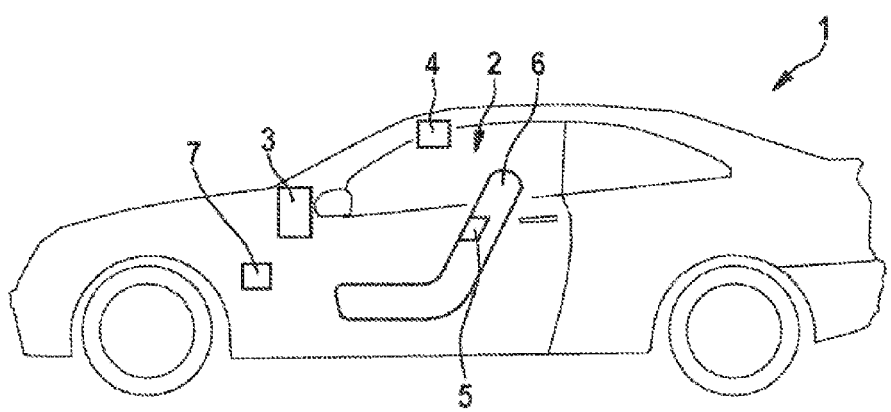
FIG. 1 shows a schematic illustration of a motor vehicle having an assistance system and one or more odor sensors.

FIG. 1 shows a schematic illustration of a motor vehicle 1 having an interior 2. The motor vehicle 1 comprises an assistance system 3 for executing various assistance functions in order to support the driver or other vehicle occupants during a journey of the motor vehicle 1. The assistance functions may comprise all functions relevant to a journey and/or operation of the motor vehicle 1, such as for example driver experience settings, comfort functions, in particular massage functions, lumbar support setting functions, air-conditioning functions, seat position settings, lighting functions, steering wheel settings, key assignments, entertainment system settings (preferably radio transmitters etc.) and the like.

There may be provision for one, several or all of the assistance functions to be activated when the state of the driver changes. The driver may for example become tired or the pressure state of the driver may change, for example due to a previous pressure situation, such as for example a near miss.

The state of a vehicle occupant may for example be identified by evaluating the odor given off by the vehicle occupant in question. To this end, a first odor sensor 4 is provided in the vicinity of a vehicle seat 6, for example in the roof lining, and/or a second odor sensor 5 is provided in the seat surface and/or the backrest and/or the head support of the vehicle seat 6. The first and second odor sensors 4, 5 are capable of recording an odor profile of the vehicle occupant sitting on the vehicle seat 6 in question and of transmitting corresponding information to the assistance system 3.

A reference odor sensor 7 may furthermore be provided in a ventilation system of the motor vehicle 1, this reference odor sensor being designed to record an odor profile of the ambient air fed to the interior 2 of the motor vehicle 1 as a reference odor profile. The reference odor sensor 7 may also be arranged in the interior 2 of the motor vehicle in order to record the reference odor profile of the interior air.

The odor sensors 4, 5, 7 should in particular be of the same type in order to obtain comparable odor profiles. In one alternative embodiment, the odor sensors 4, 5 are designed differently, wherein the reference odor sensor 7 is designed such that it covers at least the odorants of the other odor sensors 4, 5.

The odor sensors 4, 5, 7 may in each case be designed as electronic noses, that is to say as combined sensors for recording an odor profile consisting of several (at least two) odorants in the ambient air of the vehicle interior. The odor sensors 4, 5, 7 are furthermore suitable for detecting the concentrations of different odorants and providing information about an odor profile.

The recorded odor profiles may be analyzed and recorded in the assistance system 3, and a particular user may be identified as vehicle occupant through comparison with reference odor profiles of different users. One or more of the assistance functions may then be performed accordingly in a manner adjusted individually to the identified user.

A change in the state of the vehicle occupant in question may furthermore be detected by evaluating a temporal history of a change in an odor profile, that is to say a change in a concentration of at least one odorant. If a particular change in the odor profile is detected through comparison with predefined reference patterns, then it is possible to draw a conclusion as to fatigue or the occurrence of a pressure state of the driver or a further vehicle occupant. Assistance functions may accordingly generate warnings depending on the odor profile or on a change in the odor profile, execute interior functions for a vehicle occupant, such as for example activate or set a massage function in a vehicle seat, give off odorants from a corresponding odor source or control interior lighting in terms of a light color, a light intensity and/or spatial distribution, or intervene in the driving or the vehicle properties of the motor vehicle 1 in another way.

Figure 2:
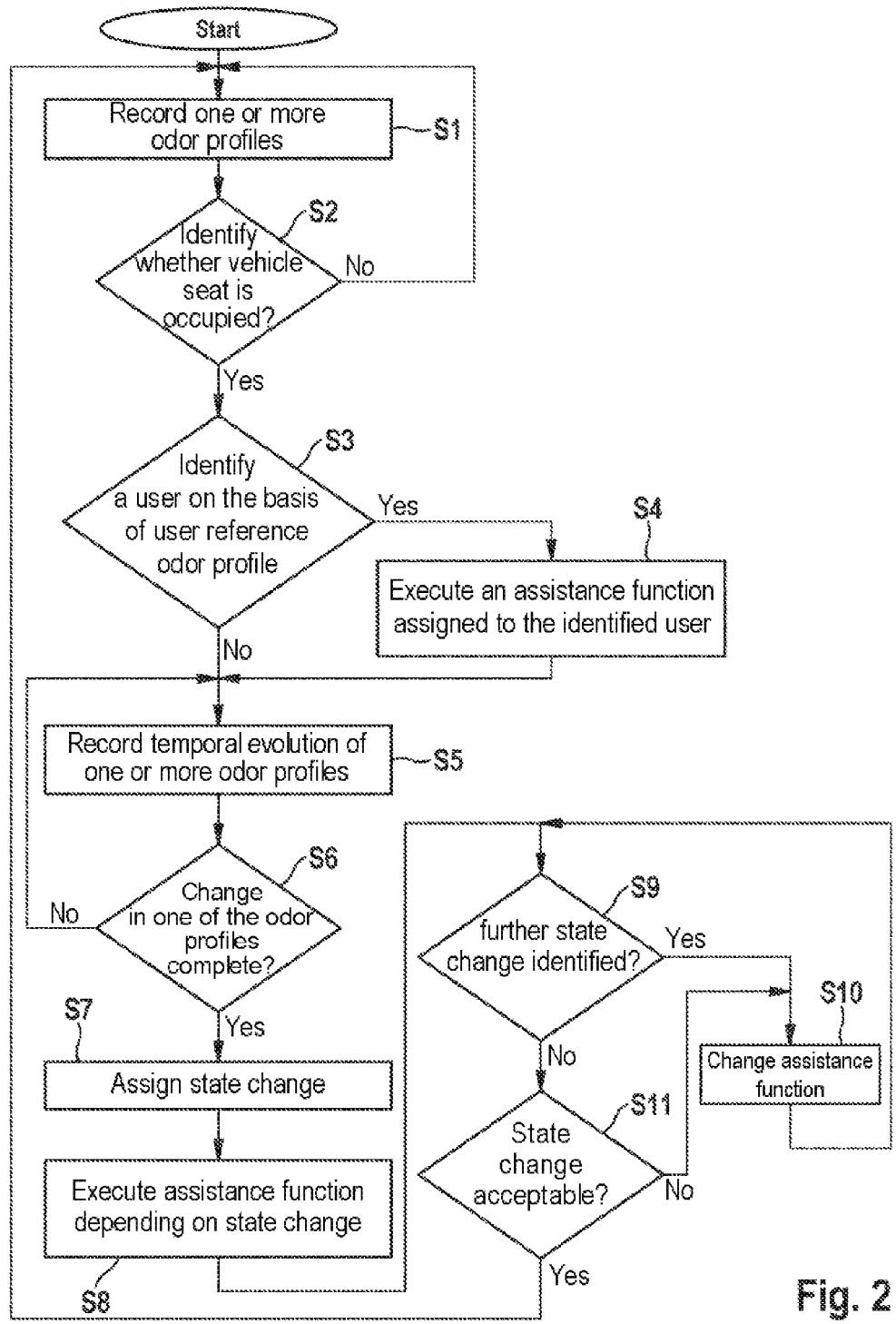
FIG. 2 shows a flowchart for illustrating an operating method in the assistance system.

A method as explained in more detail by the flowchart of FIG. 2 is executed in the assistance system 3.

In step S1, one or more odor profiles are first of all recorded by one or more of the odor sensors 4, 5, in particular assigned to a respective vehicle seat, and a reference odor profile is recorded by the reference odor sensor 7.

The odor profiles are analyzed in step S2 and a comparison with odor profiles of the ambient air is used to check whether the respective vehicle seat 6 assigned to the respective odor sensor 4, 5 is occupied. This may be achieved by recognizing a difference between the respective odor profile and the reference odor profile. If it is identified that at least one of the corresponding vehicle seats 6 is occupied (alternative: Yes), then the method is continued with step S3. Otherwise (alternative: No) there is a return to step S1.

The odor profiles assigned to the various vehicle seats 6, that is to say the odor profiles that have been recorded by odor sensors 4, 5 arranged at or close to the vehicle seat 6 in question, may be compared with predefined user reference odor profiles stored in the assistance system 3 in step S3. If it is recognized in this comparison that a recorded odor profile corresponds to or is similar to or is assigned to a known user reference odor profile associated with a particular user (alternative: Yes), a user sitting on the corresponding vehicle seat 6 is identified. The method is then continued with step S4.

If it is identified in step S3 that a recorded odor profile cannot be assigned to any known user (alternative: No), the method is continued directly with step S5. A recorded odor profile may optionally be stored as a user reference odor profile for later recognition of a user.

In step S4, one or more assistance functions assigned to a user thus recognized are executed, or parameters of at least one assistance function are adjusted individually to the recognized user.

In step S5, continuous recording of one or more odor profiles is started based on the recordings of the odor profiles by the odor sensors 4, 5 assigned to the vehicle seat 6 recognized as being occupied. One or more temporal evolutions of odor profiles are thereby obtained.

In step S6, it is checked, for each vehicle seat 6 recognized as being occupied, whether there is a temporal change in the corresponding odor profile. If this is the case (alternative: Yes), then the method is continued with step S7. Otherwise, there is a return to step S5 or alternatively to step S1.

In step S7, the temporal change in the odor profile in question is analyzed and is assigned to a state change of the user sitting on the vehicle seat in question.

The state may correspond to the occurrence of fatigue or a change in a pressure state of the vehicle occupant in question sitting on the assigned vehicle seat 6.

In step S8, one or more assistance functions assigned to the vehicle seat 6 in question may be activated or warnings may be output depending on a recognized state change. The vehicle ventilation system may in particular be activated as an assistance function depending on the odor profile in order to reduce any unpleasant odors for other vehicle occupants.

In step S9, a further state change of the vehicle occupant may be detected after the assistance functions have been performed. This may take place depending on a change in one of the odor profiles or in another way (detection of eye movements, body temperature and the like).

The method may then be continued with step S10 (alternative: No) if no state change was achieved by performing the assistance function. Otherwise (alternative: Yes), the method is continued with step S11.

In step S10, the executed assistance function is changed or switched and there is a return to step S9.

It is checked in step S11 whether the further state change led to an acceptable state. If this is the case (alternative: Yes), then the method is continued with step S1, otherwise (alternative: No), there is a jump to step S10.

Thus, depending on the further state change brought about by performing the assistance function in step S8, it is possible to stop performing the assistance function, switch the assistance function, supplement the assistance function or change or adjust the assistance function through step S10.

Experience that indicates the state change achieved by a particular assistance function in step S8 may be stored and taken into consideration when step S8 is activated again. If it is thereby identified that the triggered assistance function did not lead to an acceptable state change, this is not assigned to the corresponding state change again. Equally, an identified state change may be assigned an assistance function that led to an acceptable state. As a result, the selection of the assistance function to be activated when a state change occurs may be dependent on the success of a previous activation of the assistance function. Thus, when the triggering state change occurs again, a previously selected assistance function may no longer be activated or be performed with changed parameters and/or settings.

Thus, for example when activating a massage function as assistance function in step S8, the massage function may continue to be applied in the case of a corresponding change (triggering the activation of the massage function) in the odor profile if a change/improvement in the state is identified as a result through a further change in the odor profile of the vehicle occupant in question. In the same way, the massage function may no longer be applied in the case of a corresponding further change in the odor profile if no further change in the odor profile or no change/improvement in the state is identified as a result.

Success of a previously triggered assistance function may thereby be judged depending on the further temporal evolution of the odor profile, and the assistance function in question may be switched off, switched, maintained or adjusted as a result thereof.

LIST OF REFERENCE SIGNS 1 motor vehicle
2 interior
3 assistance system
4 first odor sensor
5 second odor sensor
6 vehicle seat
7 reference odor sensor

What is claimed is:

1. A method for operating an assistance system in a motor vehicle, comprising the steps of:
   recording at least one odor profile by way of a respective odor sensor, wherein the at least one odor profile is defined by concentrations of at least two odorants; and
   performing one or more assistance functions depending on the at least one odor profile, wherein:
   the at least one odor profile is recorded as a temporal evolution of concentrations of the odorants of the at least one odor profile,
   a change in the at least one odor profile is recognized depending on the temporal evolution of the concentrations of the odorants of the at least one odor profile,
   the change in the at least one odor profile is used to determine a change in a physiological state of a user in the motor vehicle,
   the change in the physiological state of the user is used to determine the one or more assistance functions that are performed, and
   the one or more assistance functions are performed depending on the change in the physiological state of the user.

2. The method according to claim 1, wherein
   at least two odor sensors are assigned to different vehicle seats of the motor vehicle, such that an odor profile of a user sitting on the respectively assigned vehicle seat is able to be recognized,
   seat occupancy is recognized by comparing the odor profile assigned to the vehicle seat in question with a predefined reference odor profile of ambient air, and
   the one or more assistance functions are performed depending on the recognized seat occupancy.

3. The method according to claim 2, wherein
   the predefined reference odor profile is recorded by a reference odor sensor, and
   a temporal evolution of the predefined reference odor profile is recorded.

4. The method according to claim 1, wherein
   the at least one odor profile is assigned to the user by way of a user reference odor profile,
   the one or more assistance functions are performed or adjusted individually depending on the user, and
   the user reference odor profile is stored in the assistance system, retrieved from a data carrier and/or is received externally from the vehicle.

5. The method according to claim 1, wherein
   after performing the one or more assistance functions depending on the change in the physiological state of the user, the performance of the one or more assistance functions is stopped or the performance of the one or more assistance functions is adjusted depending on a further change in the at least one odor profile.

6. A system in a motor vehicle, comprising:
an assistance system configured to execute processing to:
record at least one odor profile by way of a respective odor sensor, wherein the at least one odor profile is defined by concentrations of at least two odorants;
perform one or more assistance functions depending on the at least one odor profile, wherein:
the at least one odor profile is recorded as a temporal evolution of concentrations of the odorants of the at least one odor profile,
a change in the at least one odor profile is recognized depending on the temporal evolution of the concentrations of the odorants of the at least one odor profile,
the change in the at least one odor profile is used to determine a change in a physiological state of a user in the motor vehicle,
the change in the physiological state of the user is used to determine the one or more assistance functions that are performed, and
the one or more assistance functions are performed depending on the change in the physiological state of the user.

7. A motor vehicle, comprising:
an assistance system configured to execute processing to:
record at least one odor profile by way of a respective odor sensor, wherein the at least one odor profile is defined by concentrations of at least two odorants;
perform one or more assistance functions depending on the at least one odor profile; and
a vehicle seat; wherein:
the respective odor sensor is arranged in the vehicle seat or assigned to an area in a vicinity of the vehicle seat,
the at least one odor profile is recorded as a temporal evolution of concentrations of the odorants of the at least one odor profile,
a change in the at least one odor profile is recognized depending on the temporal evolution of the concentrations of the odorants of the at least one odor profile,
the change in the at least one odor profile is used to determine a change in a physiological state of a user in the motor vehicle,
the change in the physiological state of the user is used to determine the one or more assistance functions that are performed, and
the one or more assistance functions are performed depending on the change in the physiological state of the user.

8. The motor vehicle according to claim 7, wherein the odor sensor is arranged in a backrest, a head support or a seat surface of the vehicle seat.

9. The motor vehicle according to claim 7, wherein
the odor sensor is arranged in a roof lining in the vicinity above the vehicle seat.

10. The motor vehicle according to claim 7, further comprising:
a reference odor sensor configured to record a reference odor profile of ambient air fed into an interior of the motor vehicle.

* * * * *